(12) United States Patent
Shinogi et al.

(10) Patent No.: US 6,394,960 B1
(45) Date of Patent: May 28, 2002

(54) PULSE WAVE DETECTING DEVICE AND METHOD FOR MANUFACTURING THE SAME, AND PORTABLE WRIST DEVICE

(75) Inventors: Masataka Shinogi; Takashi Kamimoto; Hiroyuki Muramatsu; Hiroshi Odagiri, all of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/516,988

(22) Filed: Mar. 1, 2000

(51) Int. Cl.[7] .............................. A61B 5/03; A61B 8/00
(52) U.S. Cl. ...................... 600/503; 600/502; 600/500; 600/438; 600/459
(58) Field of Search ................. 600/500, 501, 600/502, 503, 323, 407, 344, 437, 438, 449, 453, 454, 455, 459, 474, 480, 481; 601/2; 73/624, 625, 627; 23/25.35; 310/311, 313 A, 313 B, 313 D (56) References Cited

U.S. PATENT DOCUMENTS

| | | | | |
|---|---|---|---|---|
| 4,086,916 A | * | 5/1978 | Freeman et al. | 600/453 |
| 4,181,120 A | * | 1/1980 | Kunii et al. | 600/459 |
| 4,413,629 A | * | 11/1983 | Durley, III | 600/453 |
| 4,771,790 A | * | 9/1988 | Yamasawa et al. | 600/499 |
| 4,920,966 A | * | 5/1990 | Hon et al. | 600/459 |
| 5,078,149 A | * | 1/1992 | Katsumata et al. | 600/459 |
| 5,409,010 A | * | 4/1995 | Beach et al. | 600/455 |
| 5,598,845 A | * | 2/1997 | Chandraratna et al. | 600/459 |
| 5,817,008 A | * | 10/1998 | Rafert et al. | 600/323 |
| 6,048,323 A | * | 4/2000 | Hon | 600/588 |
| 6,142,948 A | * | 11/2000 | Toda | 600/459 |
| 6,228,034 B1 | * | 5/2001 | Voss et al. | 600/485 |

* cited by examiner

Primary Examiner—Kevin Shaver
Assistant Examiner—Navin Natnithithadha
(74) Attorney, Agent, or Firm—Adams & Wilks

(57) ABSTRACT

In a pulse wave detecting device for detecting a pulse wave by use of an ultrasonic wave, in order to prevent attenuation of the ultrasonic wave caused by a gap formed between the pulse wave detecting device and the user's skin, a transmitter for generating an ultrasonic wave and a receiver are formed on a support substrate so as to protrude therefrom. Consequently, the transmitter and receiver contact a surface of the skin and no gap is formed between the surface of the skin and the pulse wave detecting device. A pulse wave detecting device high in detection accuracy is thus realized without the need for applying a gel between the skin and a detecting surface of the device.

23 Claims, 7 Drawing Sheets

PRIOR ART

PRIOR ART

PULSE WAVE DETECTING DEVICE AND METHOD FOR MANUFACTURING THE SAME, AND PORTABLE WRIST DEVICE

BACKGROUND OF THE INVENTION

The present invention relates generally to pulse wave detecting devices and, more particularly, to a pulse wave detecting device for detecting a pulse wave by transmitting and receiving an ultrasonic wave to and from an artery.

It is common practice to detect a pulse wave from blood flow through an artery, at medical sites or in health care. Pulse wave detection is broadly conducted by electronically, automatically detecting a pulse frequency by using a pulse wave detecting device, besides detecting of a pulse frequency per a given time through palpation.

The devices which electronically detect a pulse wave and acquire a pulse frequency include those having a piezo-type piezoelectric element that is to be positioned as a sensor over an artery in order to detect a pulse frequency from a pressure change of a surface skin caused due to a an artery pressure change (surface skin displacement by pressure). There also exist those which detect a pulse frequency through use of an ultrasonic wave.

The pulse wave detecting devices using an ultrasonic wave includes those utilizing the Doppler effect due to blood flow, as proposed, e.g. in Japanese Patent Laid-open No. 214335/1989 and U.S. Pat. No. 4,086,916. That is, a change of frequency or phase in reflection wave can be detected by transmitting an ultrasonic wave toward an artery and receiving a reflection wave thereof by a receiving element. That is, while the artery is being expanded by a blood flow, a surface of the artery approaches the transmission source and receiving element, resulting in frequency increase due to the Doppler effect. Conversely, while the artery is contracting the frequency decreases. By detecting such a frequency or phase change, it is possible to detect a pulse wave and further a pulse frequency and blood flow velocity.

Figure 2:
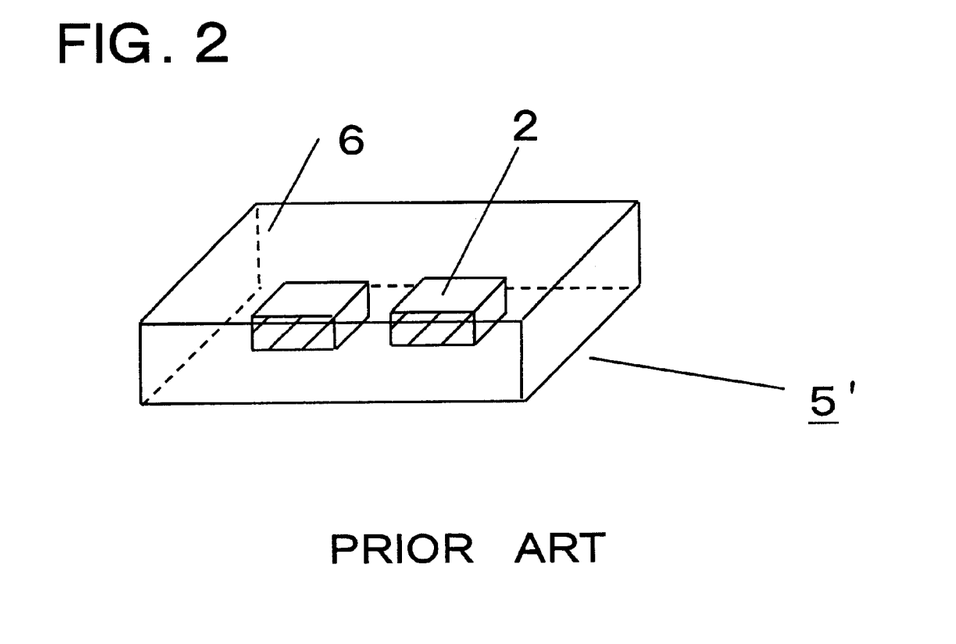
FIG. 2 is an external view showing a structure of a conventional pulse wave detecting device.

FIG. 2 shows a conventional pulse wave detecting device 5'. This structure has piezoelectric materials 2 forming an oscillation element to transmit an ultrasonic wave toward an artery and a receiving element to receive a reflection wave thereof. The piezoelectric materials 2 are covered with a resin 6.

In the conventional pulse wave detecting device, the ultrasonic wave transmitter and receiver are encapsulated by resin. When the pulse wave detecting device is put on a skin surface to detect pulsation, a gap delicately occurs between the surface skin and the pulse wave and air intrudes therein resulting in attenuation in an ultrasonic wave. It has been a conventional practice to apply gel between the surface skin and the pulse wave detecting device in order to prevent ultrasonic wave attenuation. However, such a method of applying gel between the surface skin and the pulse wave detecting device requires labor and time, including gel re-application when the ultrasonic wave again attenuates.

Meanwhile, in the conventional pulse wave detecting device, the resin-encapsulated transmitter and receiver are each formed by one planar PZT piezoelectric plate. Due to this, there is an adverse effect due to an angle given by the transmitter and receiver thus causing reduction of receiving sensitivity.

SUMMARY OF THE INVENTION

It is therefore an object of the present invention to provide a pulse wave detecting device which reduces noise to be caused due to attenuation of an ultrasonic wave.

Another object is to provide a structure to improve the receiving sensitivity in a pulse wave detecting device.

In accordance with the present invention, a pulse wave detecting device is provided comprising transmitting means for transmitting an ultrasonic wave toward an artery; receiving means for receiving the ultrasonic wave transmitted from the transmitting means; and wherein the transmitting means and the receiving means are provided protruding from a substrate.

That is, the transmitting means and the receiving means structurally protrude from the support substrate supporting the transmitting and receiving means. This allows the transmitting means and receiving means to be closely contacted with a surface skin of a wrist or the like without causing a slight gap. Thus, a pulse wave detecting device is realized that is less affected by noise. Accordingly, it is possible for the device to routinely detect a pulse wave while wearing it at any time in daily life.

Furthermore, at least one of the transmitting means and the receiving means is structurally covered with a matching layer formed of a resin or the like. This realizes a pulse wave detecting device which is highly matched in acoustic impedance and hence reduced in ultrasonic wave attenuation.

Also, a flexible board formed with a conductor pattern on a resin substrate may be used in place of the matching layer. That is, the flexible board realizes at the same time the matching of acoustic impedance by the resin substrate and the applying of an electric field to the transmitting means or receiving means by electrically connecting the conductor pattern to the transmitting or receiving means.

Also, isolation is structurally provided in the substrate mounting the receiving means and transmitting means. This provides a structure which prevents transmission of an ultrasonic wave generated by the transmitting means to the receiving means.

Also, the substrate uses a material designed to readily attenuate a ultrasonic wave. This enables efficient propagation of an ultrasonic wave toward an artery.

Furthermore, the transmitting means or the receiving means is made in an arcuate form. This eliminates the necessity to exactly adjust a parallelism between the transmitting means and the receiving means, facilitating ease of manufacture.

As described above, because the pulse wave detecting device is simple in structure, it can be routinely used by incorporating the pulse wave detecting device, for example, in a timepiece. In such a case, the transmitting means used for the timepiece can be partly utilized also as transmitting means for the pulse wave detecting device, further simplifying the structure.

Also, in the invention the transmitting means and the receiving means form one pair to provide a plurality of pairs on the support substrate. That is, although pulse wave detection is possible with one transmitter/receiver pair, a structure having a plurality of such pairs of detecting means enhances detectability of pulsation.

Also, an output means is structurally provided which acquires a pulse frequency as information about a pulse wave and outputs a pulse frequency. That is, pulsation is to be routinely checked.

Furthermore, a method for manufacturing a pulse wave detecting device is provided comprising a step of forming an electrode on a substrate and a process of selectively blowing ultrafine particles of a piezoelectric material onto the electrode to form a transmitter or a receiver.

DETAILED DESCRIPTION OF THE PREFERRED EMBODIMENT

Preferred embodiments of pulse wave detecting device of the present invention will now be described in detail with reference to the drawings.

(1) Outline of the Embodiments

The pulse wave detecting device is structured by a substrate formed with an electrode (lower electrode), piezoelectric materials bonded thereon through bonding means, and an electrode (upper electrode) formed on the piezoelectric materials. That is, transmitting/receiving means structured of a piezoelectric material is bonded to the substrate to thereby provide a structure in which the transmitting/receiving means protrudes from a surface of the substrate. The protruding transmitting/receiving means is contacted with a wrist skin to detect a blood flow through a blood vessel at the underneath of the skin. The protruding transmitting/receiving means can avoid attenuation caused by air because its structure easy to contact with skin.

By voltage application to the upper and lower electrodes, the piezoelectric material (transmitting means) generates an ultrasonic wave. The generated ultrasonic wave is radiated to a blood vessel to measure a frequency shift due to a Doppler effect caused by a blood flow through the blood vessel.

The adoption of such a structure and manufacturing method realizes higher sensitivity of pulse wave detection.

Embodiment 1

Figure 1:
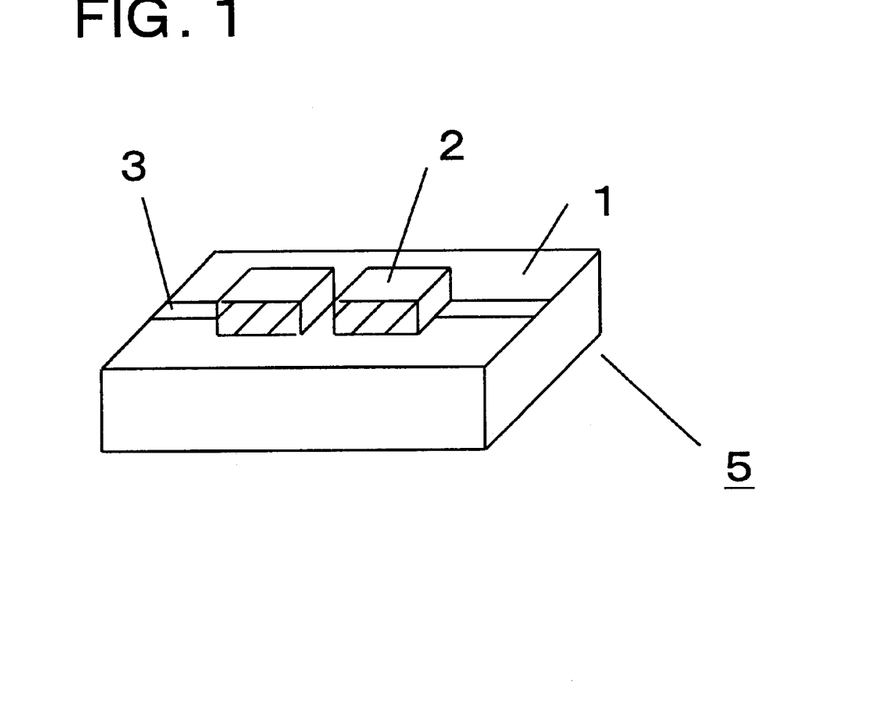
FIG. 1 is an external view showing an outline of a pulse wave detecting device according to the present invention.

Referring to FIG. 1, there is shown a structure of a pulse wave detecting device 5 of the invention. A substrate 1 is formed thereon with an electrode 3 on which PZT piezoelectric materials 2 are bonded. Furthermore, an upper electrode, not shown, is formed on the piezoelectric materials 2. This provides a structure in which an ultrasonic wave is generated by applying a voltage between the electrode 3 and the upper electrode.

An electrode in this embodiment was formed by photolithography. The electrode used a material of platinum. The substrate 1 supporting the piezoelectric materials 2 had a size of 10 mm in length, 5 mm in width and 0.5 mm in thickness. The PZT piezoelectric material 2 used a size of 2 mm in length, 1.5 mm in width and 0.2 mm in thickness.

The principle of detection in the invention includes use of the piezoelectric material to transmit an ultrasonic wave toward an artery and receive a reflection wave thereof by a receiving element thereby detecting a change of frequency or phase in the reflection wave. That is, a Doppler effect is utilized to catch a slight change of frequency to detect a pulsation. From this pulse wave a pulse frequency is acquired as information about a pulse wave. The acquired pulse frequency can be displayed on a display part. Meanwhile, for information acquiring process on a pulse wave, the pulse wave is A/D-converted and stored in a memory so that a waveform thereof can be displayed as an image or outputted to any kind of an external device such as a personal computer, medical diagnosis device or the like.

Figure 3:
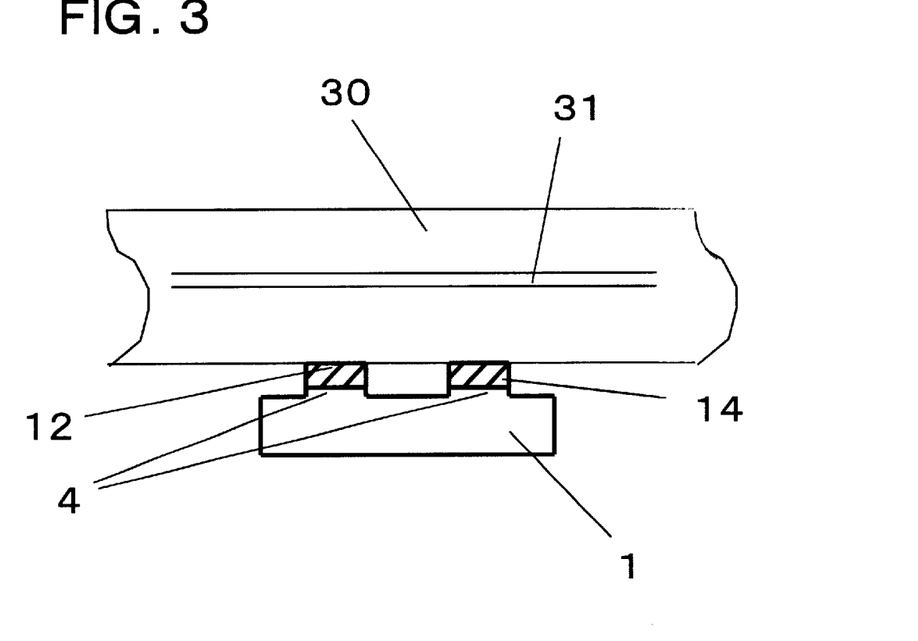
FIG. 3 is a schematic structure typically depicting pulse detection using the pulse wave detecting device of the invention.
Figure 4:
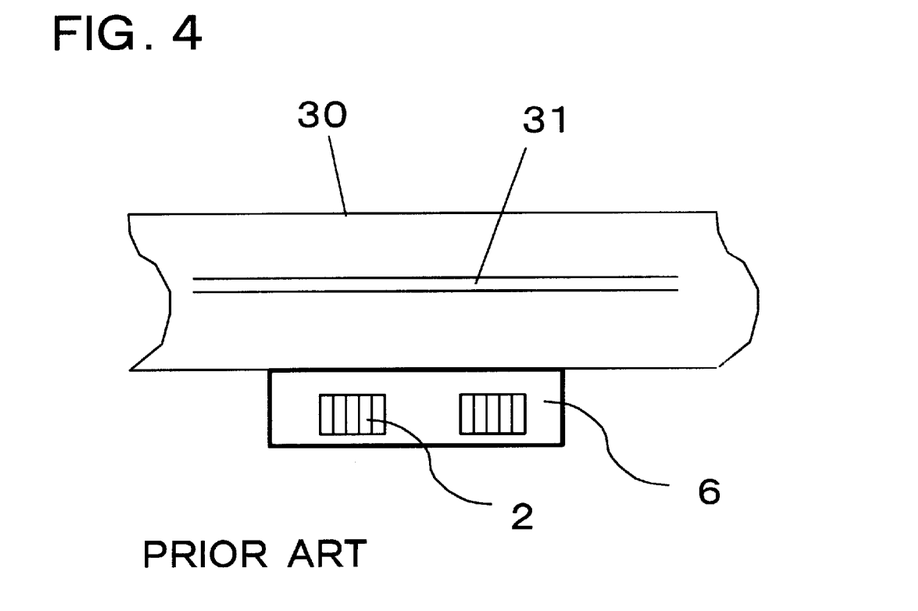
FIG. 4 is a schematic structure typically depicting a detecting part using a conventional pulse wave detecting device.

Referring to FIGS. 3, 5, 6 and 7A–7D, explanations will be made of characteristics of the pulse wave detecting device of the present embodiment. The detector (pulse wave detecting device) of the present embodiment has a structure in which a support substrate having thereon a protruding transmitter 12 and receiver 14 (FIG. 3). This structure is provided by roughly the following two ways. That is, the methods include one to previously form protrusions 4 on a substrate 1 and bond respective piezoelectric materials 2 for a transmitter and a receiver, and the other to utilize the thickness of piezoelectric materials 2 in providing protrusions on a substrate. In the present embodiment, it was desired to provide protrusions with a thickness of approximately 1 mm. Accordingly, protrusions with a thickness of 0.8 mm were previously provided on the support substrate and 0.2-mm PZT piezoelectric members were bonded to the protrusions. An embodiment of a pulse wave detecting device using such a structure of a detecting part is explained with reference to FIG. 3. FIG. 3 depicts that a pulse wave detecting device (detector) contacted with a wrist transmits an ultrasonic wave toward an artery 31. In the present embodiment, the transmitter 12 and receiver 14 are in direct contact with the wrist without causing a gap, reducing attenuation due to air. In contrast, where using a conventional pulse wave detecting device as was shown in FIG. 2, it has an increased contact area with the wrist as shown in FIG. 4 resulting in an increased possibility of causing a gap. This tends to attenuate an ultrasonic wave due to air present in the gap. In order to prevent this, there is a need to apply gel between the detecting device and the skin thus requiring time and labor. In the present embodiment, it is easy for the transmitter and receiver to be maintained in contact with the wrist. Thus, there is less possibility of attenuating an ultrasonic wave due to air, thus providing a favorable characteristic. Note that a preferred result is obtainable where the transmitter and receiver are covered with a coat material, such as a resin coat. Such a coat material is useful in protecting the piezoelectric material for the transmitter and receiver.

As explained above, the use of the invention facilitates to detect a pulsation, making possible to realize a small-sized portable device used for health care such as on a body condition during exercise.

Embodiment 2

Figure 5:
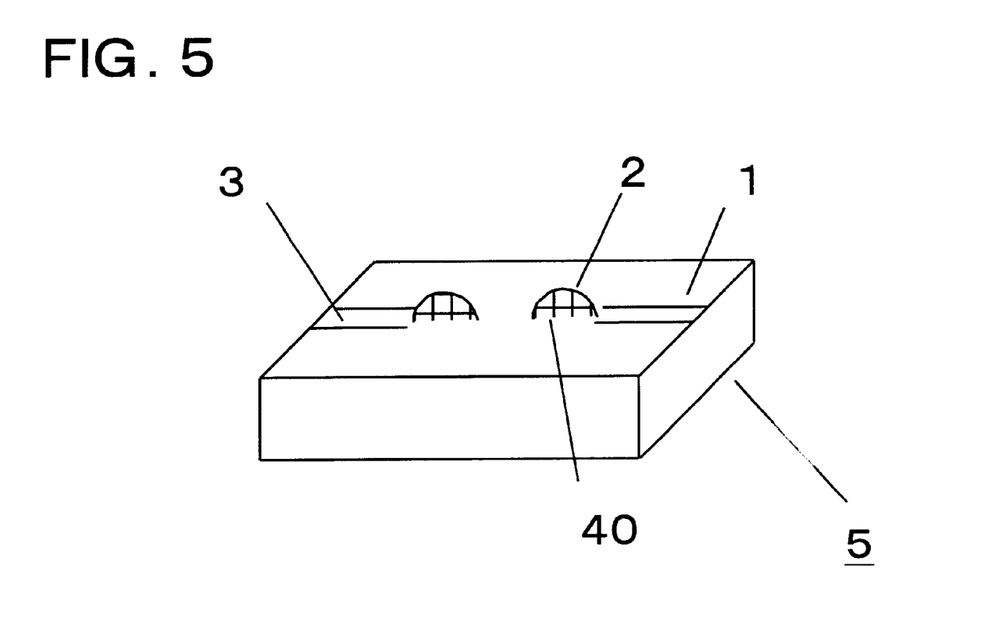
FIG. 5 is a perspective view depicting a structure of a pulse wave detecting device according to another embodiment of the invention.
Figure 6:
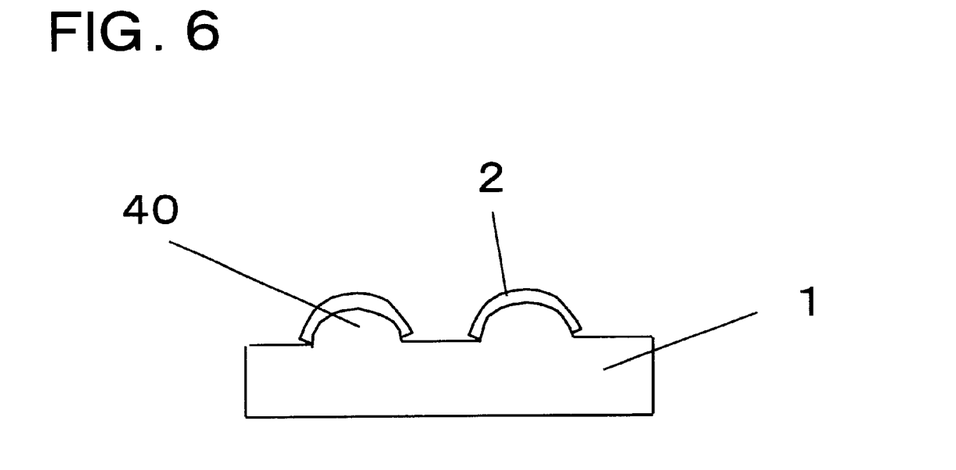
FIG. 6 is a sectional view depicting a longitudinal sectional structure of the pulse wave detecting device according to the other embodiment of the invention.

Another embodiment is given wherein a structure having transmitting means and receiving means at least one of which is formed in an arcuate form. FIG. 5 shows a pulse wave detecting device of this embodiment, and FIG. 6 shows a sectional view thereof. The pulse wave detecting device 5 of the invention has a structure having an arcuate protrusion (arcuate protrusion 40) formed on a substrate and electrodes 3 formed in planar and protruding areas on the substrate. Furthermore, ultra-fine particles of a piezoelectric material are formed on the protrusions. In this manner, the protrusions on the substrate may be formed in an arcuate concave form to have a piezoelectric material thereon. Alternatively, a piezoelectric material may be formed in an arcuate convex form on a planar surface of a substrate or the protrusion or piezoelectric material may be in a concave form.

Herein, an upper electrode, not shown, is further formed on the piezoelectric material 2. The application of a voltage to between the electrode 3 and the upper electrode generates an ultrasonic wave.

In the present embodiment, the electrode 3 was formed by photolithography using a support substrate 1 having a size of 10 mm in length, 5 mm in width and 0.5 mm in thickness. The substrate used was a resin substrate. The pulse wave detecting device of the present embodiment is used to generate an ultrasonic wave for detecting pulse waves.

A detecting part of the present embodiment (pulse wave detecting device) is explained on its characteristic, with reference to FIG. 6. The detecting part (pulse wave detecting device) has a structure in which a substrate 1 having an arcuate protrusion 40 on which a piezoelectric material 2 is formed so that a voltage can be applied between electrodes to generate an ultrasonic wave. In this embodiment both the receiver and transmitter comprise a piezoelectric material 2 formed on the arcuate protrusion 40. It is natural to provide an arcuate form only to the receiver.

The provision of piezoelectric material on the arcuate protrusion 40 enhances receivability and improves receiving sensitivity. This further improves the detectability upon wearing a portable wrist device having the pulse wave detecting device and realizes a pulse wave detecting device less susceptible to adverse effects due to body motion.

Figure 7A:
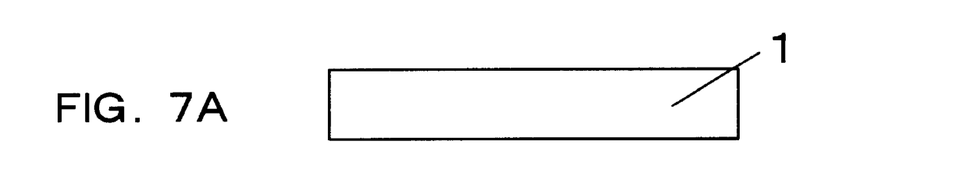
FIGS. 7A to 7D are a process view showing a method for manufacturing a pulse wave detecting device of the invention.
Figure 7B:
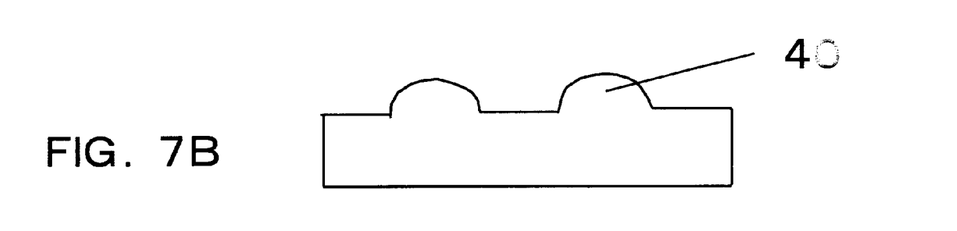
Figure 7C:
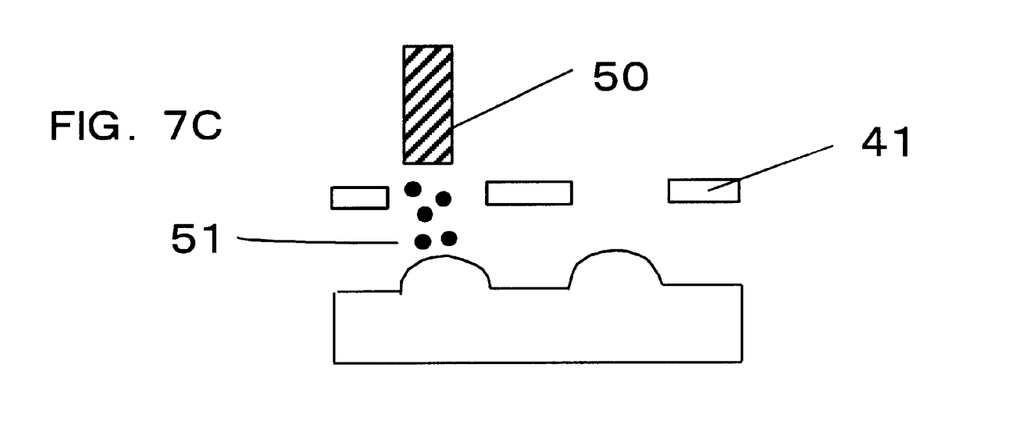
Figure 7D:
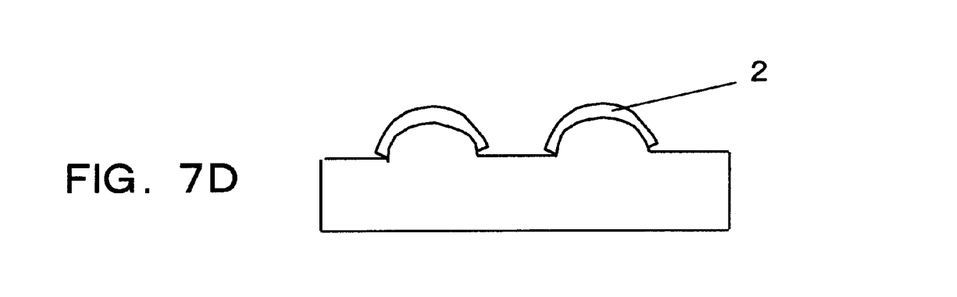

A method for manufacturing an arcuate protrusion as described above will now be described with reference to FIG. 7. First, in a first process step (FIG. 7A) a substrate 1 was prepared. In this embodiment, a resin substrate was used. In a second process step (FIG. 7B) an arcuate protrusion 40 is formed by cutting or the like. In a third process (FIG. 7C) a mask 41 is set up in a position aligned with the arcuate protrusion 40 on the substrate to blast ultra-fine particles 51 of a piezoelectric material through a nozzle 50, thereby forming a piezoelectric material on the arcuate projection 40. Ultra-fine particles with a diameter of 0.3 mm where used herein. In this manner, as shown in FIG. 7D a piezoelectric material 2 was formed by depositing ultra-fine particles on the arcuate protrusion 40. This method is particularly effective to form a piezoelectric material on a non-planar substrate where forming a piezoelectric material to a particular shape, such as an arcuate form. This method is of course applicable also for forming a piezoelectric material of a pulse wave detecting device structured as was shown in FIG. 1.

Furthermore, a resin coat if provided covering the piezoelectric material serving 2 protects the piezoelectric material as a transmitter and receiver. This structure also provides a favorable result of pulse detection.

Incidentally, although the pulse wave detecting device was realized by the method of forming a piezoelectric material on the convex arcuate protrusion, a similar effect is obtainable for a convex form.

Embodiment 3

Figure 8:
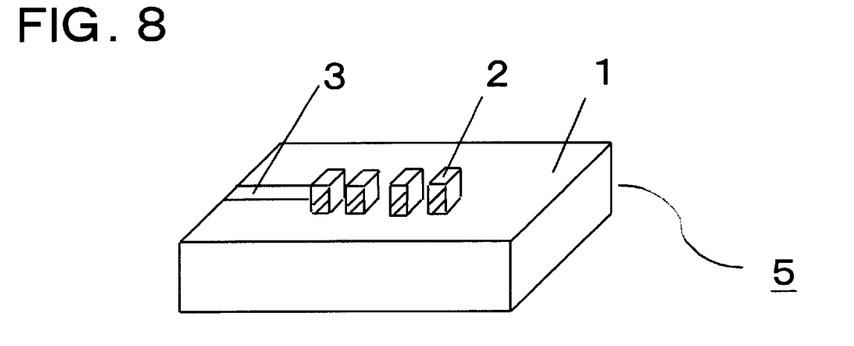
FIG. 8 is a perspective view depicting a pulse wave detecting device mounting a plurality of detecting parts.

FIG. 8 shows an embodiment mounted with a plurality of detecting parts structured as in the above embodiment. That is, a plurality of pairs of piezoelectric materials are mounted on a resin substrate 1 in order to perform transmission and reception. With this structure, an intense portion of a pulse wave can be extracted for selective transmission and reception, obtaining an optimal pulse wave signal. This also provides an effect of easily detecting a pulse wave even if positioned without care.

Embodiment 4

Figure 9:
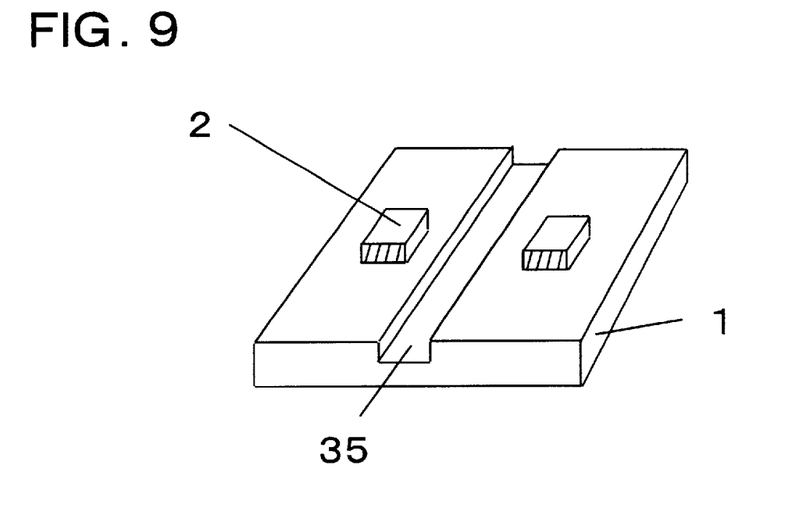
FIG. 9 is a perspective view depicting a pulse wave detecting device having a groove formed in a support substrate.

FIG. 9 shows a structure having a separator layer formed between transmitting means and receiving means in a substrate, in order not to convey ultrasonic wave vibration. That is, a groove 35 is formed between the transmitting means and receiving means. This groove 35 if formed prevent an ultrasonic wave from propagating from the transmitting means through the substrate to the receiving means. Thus, the receiving means can extract a signal with a preferred S/N ratio.

Although in the present invention the support substrate was fabricated by cutting means such as dicing, the groove 35 may be formed by other means. Meanwhile, if an absorber member is formed in the groove to absorb vibration, the propagation can be reduced. According to this invention, a frequency shift due to a Doppler effect can be detected, Meanwhile, it is possible to obtain a further effect by injecting into the groove 35 a material for absorbing propagation vibration, such as a gel material.

Embodiment 5

Figure 10:
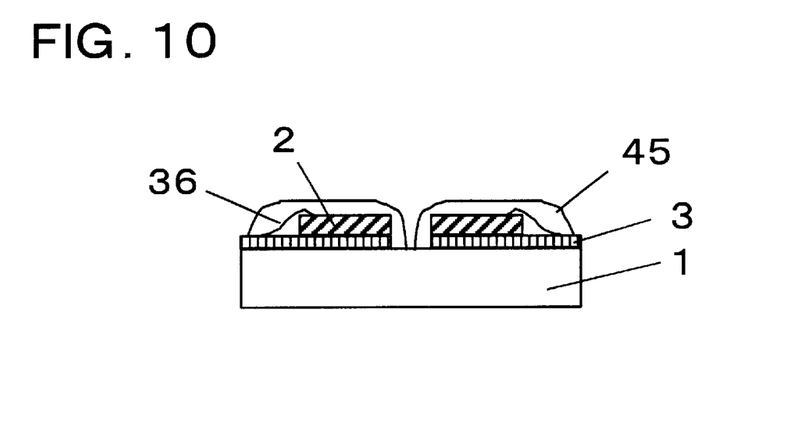
FIG. 10 is a sectional view of a pulse wave detecting device of the invention.

A matching layer 45 is formed on the piezoelectric material 2 to provide acoustic impedance matching between the piezoelectric material and the wrist, thus preventing an ultrasonic wave from attenuating. The matching layer 45 may be provided on any one of the transmitting means and receiving means formed of a piezoelectric material.

FIG. 10 shows a structure having matching layers 45 formed respectively on the transmitting means and the receiving means, in order to achieve impedance matching to the wrist. The formation of matching layer 45 realizes a pulse wave detecting device having an attenuation-reduced characteristic.

Incidentally, in the present embodiment electrical connection is made by bonding wires 36 between an upper electrode and an extension electrode (interconnection) provided on the substrate, in order to apply an electric field to the piezoelectric materials. After wire bonding, a matching layer 45 is formed thus realizing a pulse wave detecting device. Incidentally, the matching layer is mad e by molding using a resin.

Figure 11:
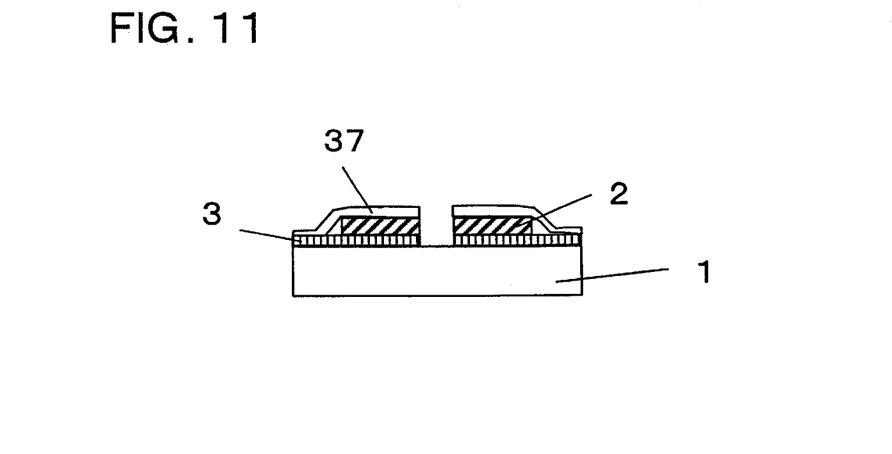
FIG. 11 is a sectional view of a pulse wave detecting device of the invention.

Meanwhile, as s how n in FIG. 11, a conductive member such as a flexible board 37 formed with a conductor pattern on a resin layer may be used to realize wire connection between the upper electrode on the piezoelectric material 2 and an interconnection on the substrate. This provides a similar effect. That is, the role of the matching layer is performed by the resin layer of the flexible board while the role of the wire is forformed by the conductor pattern. Also, where using such a flexible board, electrical connection can be provided through a conductor pattern between a top surface of the piezoelectric material and an interconnection on the substrate without requiring the formation of an upper electrode on the piezoelectric material. In this manner, the use of a flexible board formed with a conductor pattern on a resin layer makes it possible to realize a compact, thin pulse wave detecting device.

Embodiment 6

The substrate 1 used in the invention has a piezoelectric material disposed thereon which oscillates to propagate vertical vibration toward an artery, and requires a characteristic sufficient not to propagate the vibration through the substrate. Consequently, the substrate material preferably has an characteristic to attenuate a ultrasonic wave. The present embodiment used a resin substrate, and more specifically a plastic material such as a porous material. Of course, a non-porous material may be used. The use of a material having a characteristic to attenuate an ultrasonic wave in this manner realizes a high sensitivity pulse wave detecting device.

Embodiment 7

Figure 12:
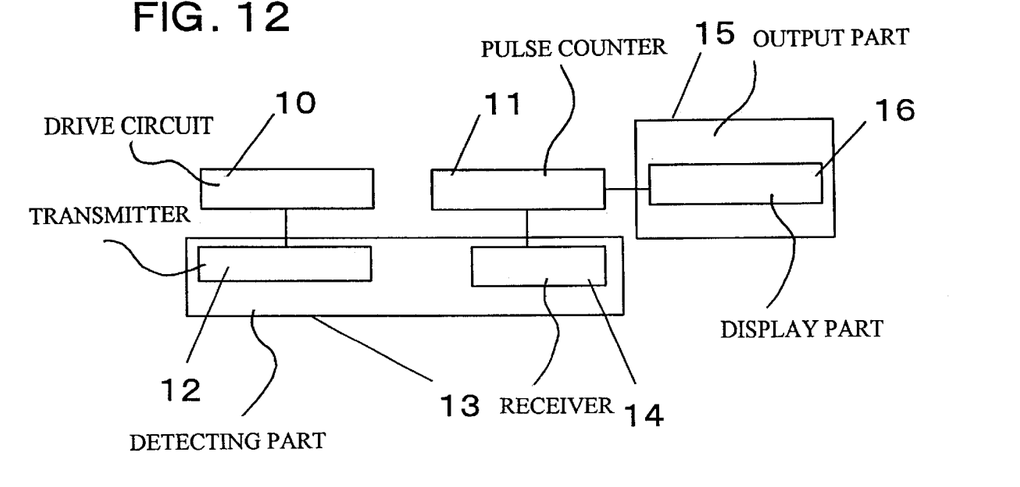
FIG. 12 is a block diagram showing a structure of a portable wrist device for detecting pulsation.

Portable wrist devices using a pulse wave detecting device according to the above embodiments will be explained with reference to FIGS. 12 to 14. As shown in FIG. 12, a portable wrist device mounting a pulse wave detecting device has a detecting part (pulse wave detecting device) 13 and an output part 15.

The detecting part 13 has a transmitter 12 to be positioned on a human body surface and a receiver 14 to be positioned over an artery of a body surface near the transmitter 12. A drive circuit 10 is also provided to generate an ultrasonic wave by driving the transmitter 12. The transmitter 12 is positioned over an artery to transmit an ultrasonic wave at 9 MHz toward the artery. The oscillation at 9 MHz is well matched to a human body, making it possible to easily detect a pulse wave.

The receiver 14 receives an ultrasonic wave transmitted from the transmitter 12 and propagated through the human body including an artery, and delivers a reception signal to a pulse counter 11. A display part displays an output from the pulse counter 11. Incidentally, the transmitter 12 and the receiver 14 are packaged in a common part as a pulse wave detecting apparatus (pulse wave sensor) 13 so that they can be positioned on a body surface over an artery.

The output part 15 includes a display part 16 to display a pulse frequency sent from the pulse counter 11. The display part 16 is structured by a liquid crystal display to display an image of pulse frequency. Alternatively, a pulse frequency may be electrically displayed on a panel.

Figure 13:
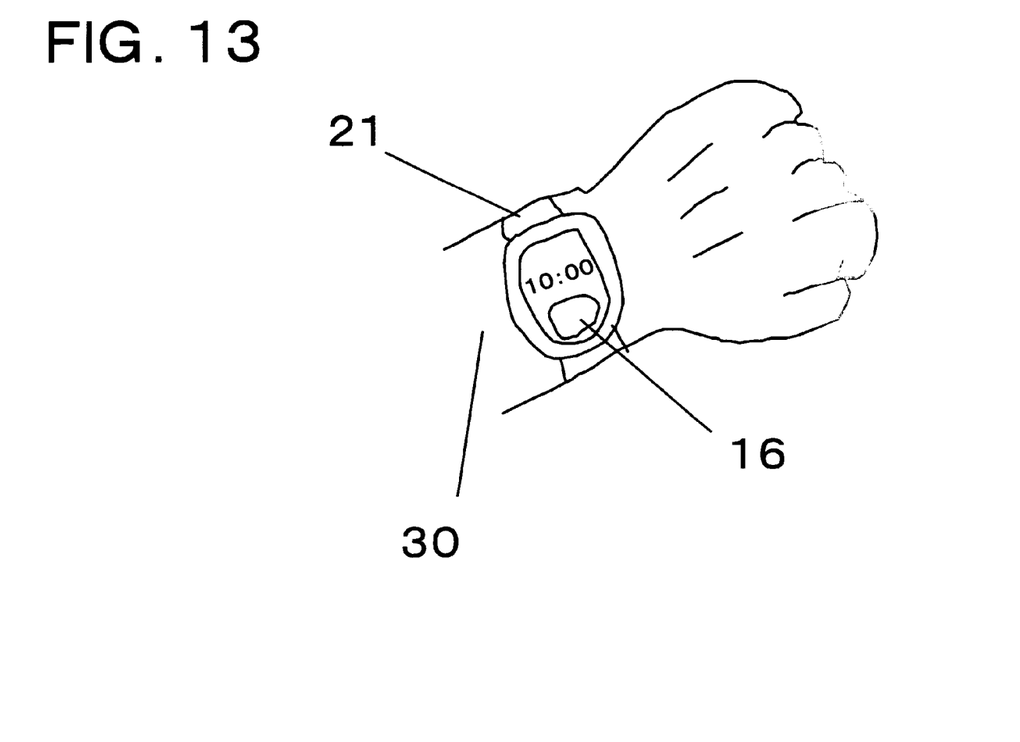
FIG. 13 is an external view showing a state the portable wrist device of the invention is worn on a wrist.

FIG. 13 shows a manner of wearing on a wrist 30 a portable wrist device mounting a pulse wave detecting device of the invention. The wrist portable device has a function to display a pulse frequency on the pulsation display part 16.

Figure 14:
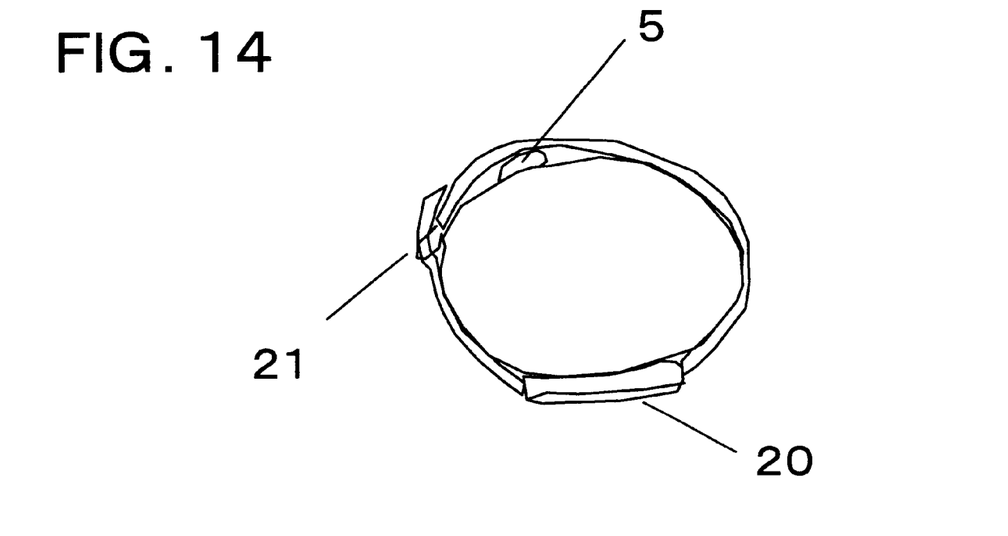
FIG. 14 is an external view of a portable wrist device having a pulse wave detecting device of the invention.

FIG. 14 depicts a state that a pulse wave is detected by a pulse wave detecting device built in a watch. As shown in the figure, the watch (wrist portable device) has a watch main body and a strap 21 wherein a pulse wave detecting device 5 is mounted at an inside of the strap. The watch main body is put on a back side of a left (or right) wrist, similarly to a usual watch. In such a case although no position is shown for the pulse wave detecting device (sensor), it is possible to move and adjust the sensor lengthwise of the strap to a position over a radial artery.

On the pulse wave detecting device (sensor) 5, a transmitter 12 and a receiver 14 are arranged in a direction perpendicular to the direction of the strap such that they are to be positioned along a radial artery, i.e. the transmitter is on the hand tip side and the receiver on the shoulder side. Incidentally, the transmitter 12 and the receiver 14 may be inverted in position.

The sensor, a drive circuit of the watch main body, and a pulse wave detecting circuit are connected through wiring built in the strap.

The watch main body has a display surface (dial) 20 having a timepiece display part to display as a timepiece a time (day, day of the week) and a pulse wave display part 16 to display a pulse frequency and pulsation.

A pulse counter 11 is made to supply a pulse signal to the display part each time a pulse waveform peak is detected. Depending on an output of such a pulsation signal, the pulsation display part 16 flickers in green. Seeing a flicker of the pulse display section, the user can visually recognize his or her pulse wave.

Incidentally, the flicker color of the pulsation display part 16 maybe changed depending on a pulse frequency, e. g. a pulse frequency of 69 and less by yellow flicker, 70 to 90 by blue flicker, 91 to 110 by green flicker, 111 to 130 by orange flicker, and 131 and higher by red flicker.

According to t he pulse wave detecting device of the invention, the ultrasonic wave transmitting part and receiving part for detecting pulsation can be closely contacted with a wrist. It is possible to avoid attenuation in an ultrasonic wave due to air. Further, pulsation detection is easy.

Also, by making the ultrasonic wave transmitting part an d receiving part for detection pulsation in an arcuate shape, reception rate improve and pulse detecting means resistant to body movement noise can be provided.

As explained above, the use of the invention facilitates ease in detecting a pulsation, making possible to realize a small-sized portable device used for health care such as on a body condition during exercise.

What is claimed is:

1. A pulse wave detecting device comprising:
transmitting means for transmitting an ultrasonic wave toward an artery;
receiving means for receiving the ultrasonic wave transmitted by the transmitting means and reflected by the artery; and
a rigid support substrate on which the transmitting means and the receiving means are provided;
wherein the transmitting means and the receiving means protrude from a surface of the substrate, the surface being disposed while in use against a user's skin.

2. A pulse wave detecting device according to claim 1; wherein the transmitting means and the receiving means comprise piezoelectric elements.

3. A pulse wave detecting device according to claim 1; wherein the support substrate has a protrusion formed on a surface thereof, and at least one of the transmitting means and the receiving means is provided on the protrusion.

4. A pulse wave detecting device according to claim 2; wherein at least one of the transmitting means and the receiving means has an arcuate form.

5. A pulse wave detecting device according to claim 1; wherein at least one of the transmitting means and the receiving means is covered with a matching layer so as not to attenuate the ultrasonic wave.

6. A pulse wave detecting device according to claim 1; further comprising a flexible board comprising a conductor pattern formed on a resin layer; wherein the transmitting means and the receiving means each have a first surface facing the support substrate and a second surface opposite the first surface opposing the support substrate, the second surfaces of the transmitting means and the receiving means being electrically connected with the conductor pattern.

7. A pulse wave detecting device according to claim 1; further comprising a separator layer disposed on the support substrate between the transmitting means and the receiving means for reducing the transmission of vibration due to the ultrasonic wave.

8. A pulse wave detecting device according to claim 1; wherein the substrate is formed of a material effective to attenuate the ultrasonic wave.

9. A pulse wave detecting device according to claim 1; further comprising a coating material covering the transmitting means and the receiving means.

10. A pulse wave detecting device according to claim 1; wherein the transmitting means and the receiving means comprise one transmitter/receiver pair, and a plurality of the transmitter/receiver pairs are provided on the support substrate.

11. A portable wrist device comprising:
a pulse wave detecting device having transmitting means for transmitting an ultrasonic wave toward an artery, receiving means for receiving the ultrasonic wave transmitted by the transmitting means and reflected by the artery and producing a pulse wave signal, and a support substrate on which the transmitting means and the receiving means are mounted so that the transmitting means and the receiving means protrude from a surface of the support substrate, the surface being disposed while in use against a user's skin;
pulse wave information acquiring means for acquiring the pulse wave signal from the pulse wave detecting device and determining pulse wave information based on the pulse wave signal; and
output means for outputting the pulse wave information from the pulse wave information acquiring means.

12. A portable wrist device according to claim 11; wherein the pulse wave information acquiring means includes means for acquiring a pulse frequency as the pulse wave information from the receiving means, and the output means includes means for outputting the pulse frequency.

13. A pulse wave detecting device comprising: a support substrate disposable against a part of living body; a transmitter provided on the substrate as to protrude from a first surface of the substrate for transmitting an ultrasonic signal toward an artery in the living body; and a receiver provided on the substrate so as to protrude from the first surface of the substrate for receiving the ultrasonic signal transmitted by the transmitter and reflected by the artery; wherein the transmitter and the receiver protrude from the first surface of the support substrate so that when the support substrate is placed in contact with the living body, the transmitter and the receiver are urged into close contact with the living body to thereby reduce attenuation of the ultrasonic signal that may otherwise be caused by an air gap formed between the support substrate and the living body.

14. A pulse wave detecting device comprising: a support substrate disposable against a part of a living body; a transmitter having a piezoelectric device provided on the substrate so as to protrude from a first surface of the substrate for transmitting an ultrasonic signal toward an artery in the living body; and a receiver provided on the substrate so as to protrude from the first surface of the substrate for receiving the ultrasonic signal transmitted by the transmitter and reflected by the artery; wherein the transmitter and the receiver protrude from the first surface of the support substrate so that when the support substrate is placed in contact with the living body, the transmitter and the receiver are urged into close contact with the living body to thereby reduce attenuation of the ultrasonic signal that may otherwise be caused by an air gap formed between the support substrate and the living body.

15. A pulse wave detecting device according to claim 14; wherein the receiver comprises a piezoelectric device.

16. A pulse wave detecting device according to claim 14; wherein the support substrate has at least one protrusion formed on the first surface thereof, and at least one of the transmitter and the receiver is formed on the protrusion.

17. A pulse wave detecting device according to claim 16; wherein the at least one protrusion has an arcuate convex or concave form such that the at least one of the transmitter and receiver formed thereon has an arcuate form.

18. A pulse wave detecting device according to claim 14; further comprising a matching layer covering at least one of the transmitter and the receiver to reduce attenuation of the signal.

19. A pulse wave detecting device according to claim 14; further comprising a flexible circuit board comprising a conductor pattern formed on a flexible resin board; wherein the transmitter and the receiver each have surfaces protruding from the support substrate that are electrically connected with the conductor pattern.

20. A pulse wave detecting device according to claim 14; further comprising a separator provided on the support substrate between the transmitter and the receiver for preventing the transmission of vibration from the transmitter to the receiver due to signal transmission by the transmitter.

21. A pulse wave detecting device according to claim 20; wherein the separator comprises a groove formed in the support substrate.

22. A pulse wave detecting device according to claim 14; wherein the support substrate is formed of a material effective to attenuate the signal.

23. A pulse wave detecting device comprising:
a transmitter for transmitting an ultrasonic wave toward an artery;
a receiver for receiving the ultrasonic wave transmitted by the transmitting means and reflected by the artery; and
a support substrate on which the transmitter and the receiver are provided;
wherein the transmitter and the receiver protrude from a surface of the substrate, the surface being disposed while in use against a user's skin.

* * * * *